United States Patent [19]

Mach et al.

[11] Patent Number: 4,978,632
[45] Date of Patent: Dec. 18, 1990

[54] METHOD OF PRE-TREATING SAMPLES IN PEROXIDASE-CATALYZED ENZYME ASSAYS

[75] Inventors: Patrick A. Mach, Shorewood; Jeffrey A. Thompson, Richfield; Richard S. Creager, Bloomington; Cheri W. Fink, Prairie, all of Minn.

[73] Assignee: Kallestad Diagnostics, Inc., Chaska, Minn.

[21] Appl. No.: 284,541

[22] Filed: Dec. 15, 1988

[51] Int. Cl.⁵ ............... G01N 33/535; C12Q 1/28
[52] U.S. Cl. ............................ 435/7; 435/28; 435/4; 435/188; 436/66; 436/510; 436/825; 436/175
[58] Field of Search ............ 435/4, 7, 28, 188; 436/510, 825, 174, 175, 66

[56] References Cited

U.S. PATENT DOCUMENTS

| | | | |
|---|---|---|---|
| 4,292,038 | 9/1981 | Kondo et al. | 23/230 B |
| 4,299,815 | 11/1981 | Hansen et al. | 424/1 |
| 4,353,984 | 10/1982 | Yamada et al. | 435/14 |
| 4,362,531 | 12/1982 | de Steenwinkel et al. | 23/230 |
| 4,440,880 | 4/1984 | Tom | 435/7 |
| 4,587,220 | 5/1986 | Mayambala-Mwanika et al. | 436/66 |
| 4,810,630 | 3/1989 | Craig et al. | 435/7 |

OTHER PUBLICATIONS

Boscato et al., "Incidence and Specificity of Interference in Two-Site Immunoassays", 32 Clin. Chem. 1491-1495, (1986).
Nickoloff, 21 *CRC Critical Reviews and Clinical Laboratory Sciences*, 255-267.
Burns, "The Unlabelled Antibody Peroxidase-Anti-Peroxidase Method (PAP)", 1 *Techniques in Immunocytochemistry*, 91-95, (1982).

*Primary Examiner*—Esther L. Hepplinger
*Assistant Examiner*—Toni R. Scheiner
*Attorney, Agent, or Firm*—Mary P. Bauman; James R. Haller; Gregory P. Kaihoi

[57] ABSTRACT

A method for reducing the occurrence of falsely elevated results in a peroxidase-catalyzed, enzyme assay is described. Interference in an assay caused by blood or bood products in a clinical specimen is eliminated or reduced by reacting the specimen with an oxidizing agent such as sodium hypochlorite, hydrogen peroxide or sodium meta-periodate.

9 Claims, No Drawings

METHOD OF PRE-TREATING SAMPLES IN PEROXIDASE-CATALYZED ENZYME ASSAYS

FIELD OF INVENTION

This invention relates to an oxidative sample treatment to eliminate interference of blood or blood products in enzyme assays.

BACKGROUND OF THE INVENTION

The use of enzyme immunoassays (EIAs) to determine whether a particular analyte is present in a patient sample has aided the expansion of diagnostic medicine. In a typical enzyme immunoassay, an assay reagent is labeled with an enzyme, the reagent becoming bound to a solid support in an amount that depends upon the amount of analyte in the sample. Enzyme substrate, generally added in a final step of the assay, reacts with the enzyme to generate a detectable signal which is related to the amount of analyte present in the sample.

However, present in some patient samples are compounds which may interfere with enzyme activity. One form of interference occurs when an interfering compound acts to catalyze a signal generating reaction in the absence of the specific enzyme. The presence of such compounds can result in incorrect assay interpretation owing to the generation of signal in an amount unrelated to the presence of the analyte in the patient sample.

Blood or blood products (e.g., the contents of lysed red blood cells) are common sources of assay interference in enzyme assays which employ peroxidase as the enzyme label. The blood or blood products help convert the enzyme substrate to its oxidized products, giving rise to positive assay interference. Specifically, the heme component of hemoglobin can bind to solid supports used in EIAs to immobilize reagents. The heme moiety (also called "microperoxidase") present during signal development in peroxidase-catalyzed EIAs generates non-specific signal (i.e. color development) and is a source of positive interference.

SUMMARY OF THE INVENTION

It has been discovered that the positive interference in peroxidase-catalyzed enzyme assays caused by blood or blood products can be eliminated by the addition of oxidative compounds, such as sodium hypochlorite, hydrogen peroxide and sodium meta-periodate, to the patient specimen. The treated patient specimen can be used in the enzyme assay with no interfering effects.

DETAILED DESCRIPTION OF THE PREFERRED EMBODIMENT

The methods of this invention can be used with patient specimens obtained by conventional methods, such as swabs, washes, aspirates and the like, taken from the eye, the nares at the back of the nose, cervix, vagina, urethra, rectum, throat, blood, serum, plasma and the like.

In one embodiment of the invention, the oxidizing agent may be added directly to the patient sample. For example, a solution of oxidizing agent may be added to a patient sample just prior to taking an aliquot of the sample for use in the assay.

In another embodiment, the oxidizing agent solution may be added to a reagent, such as a detergent solution, that is used to extract the patient sample from a swab or the like. This extraction solution is added to a tube containing a swab sample, mixed, and allowed to incubate for a predetermined length of time, followed by expulsion of liquid from the swab. The liquid containing the patient sample is then evaluated using an EIA or other enzyme assay such as a peroxidase catalyzed enzyme assay.

In yet another embodiment, a solution of oxidizing agent is added to the liquid extracted from a patient swab using a detergent or the like. This solution of oxidizing agent and patient sample is allowed to incubate for a predetermined length of time, following which an appropriate aliquot is taken for use in the enzyme assay.

The method of this invention may be used in any enzyme assay but is particularly useful in a passive or active, capture-dependent, peroxidase-catalyzed, sandwich-type EIA. The sandwich-type EIA is preferably one in which an antibody:antigen:antibody sandwich tethered to a solid support is formed. Typically, antigen or antibody is bound to a solid support such as filter paper, test tubes made from polyethylene, polystyrene, polypropylene or other suitable materials, latex particles, glass or plastic beads, magnetic particles or the like. Patient samples are contacted with the solid support and the specific analyte being assayed binds to the anchored ligand on the solid support. A second antibody with specificity to the analyte and directly or indirectly labeled with peroxidase is added and, after the reaction mixture has been allowed to incubate for a sufficient time to allow the reaction to occur, the solid support is washed. If the second antibody is directly labeled, then, after the solid support is washed, enzyme substrate is added to the solid support and the resulting signal is measured by colorimetric or spectrophotometric techniques. If the second antibody is unlabeled, then a labeled antiglobulin directed against the second antibody may be added and the solution allowed to incubate for a predetermined time before washing and determination of the quantity of label by conventional techniques.

Although the sandwich-type assay described above utilizes antibodies and antigens, the methods of this invention may be used generally with peroxidase-catalyzed, sandwich-type assays involving ligand-receptor pair members. As used herein, "ligand receptor pair" refers to a pair of compounds of which one, a "receptor" is capable of recognizing a particular spatial and polar organization of the other ("ligand") or portion thereof, and is capable of binding to that compound. For various ligands, illustrative receptors forming the other half of a ligand-receptor pair include antibodies, enzymes, lectins, Fab fragments, complementary nucleic acids and the like.

The invention is useful in detecting a broad range of analytes. U.S. Pat. No. 4,374,925 and U.S. Pat. No. 3,817,837, the teachings of which are incorporated herein by reference, set out excellent lists of analytes which are part of specific binding pairs. Other examples of binding pairs include nucleic acids and complementary nucleic acids. Analytes of particular interest include viruses, bacteria, fungi and protozoans, specific products and assemblages thereof and macromolecules and products of living organisms.

Antibodies useful with enzyme assays may be raised in humans or non-human species such as guinea pig, goat, horse, rabbit, sheep, etc. by immunization with appropriate antigens in accordance with known methods. Monoclonal antibody to appropriate antigens may also be used with the methods of this invention.

Assay interference can be detected by comparing assay results with results obtained using other evaluation methods, i.e., culture techniques, microscopic analysis, and the like. A specific example of the interference by blood or blood products of a direct antigen EIA is described as follows in connection with an assay for the detection of *Chlamydia trachomatis*. Samples for the detection of chlamydia were taken from prospective patients. Direct fluorescent labeling techniques were used to determine whether chlamydia was present in a sample, as follows: Antibody that binds specifically to chlamydia and that was labeled with a fluorescent agent was obtained. Labeled antibody of this type is commercially available. A volume of specimen extract was obtained and centrifuged to form a pellet comprised of chlamydial organisms and debris from the sample. The pellet was resuspended in a minimal volume of buffer, spotted on a microscope slide, fixed with methanol and stained with the labeled antibody reagent. The antibody bound to the chlamydia, if any, on the slide. The slide was examined using an appropriate microscope to determine whether chlamydia were present. In samples not treated with the oxidizing agent prior to performing the EIA, a significant number of specimens that tested negative with the direct fluorescent method yielded positive EIA results in the absence of the additives described in this invention.

Functional false positive results were shown to be eliminated by treatment with an oxidizing agent such as hydrogen peroxide. Patient swab samples were treated by adding 1 ml of a sample treatment solution (containing buffer and a detergent) to the swab sample and allowed to incubate for an appropriate period of time. The sample solution was then vortexed, the swab removed and the liquid extracted from the swab was divided into equal volumes. To one of the aliquots a solution of hydrogen peroxide was added, to the other an appropriate control solution was added. The sample was then assayed for the presence of chlamydial antigen using a peroxidase-catalyzed, sandwich-type EIA. If the absorbance units at 450 nanometers (nm) for a particular EIA is greater than 0.1 O.D. plus the negative control performed at the same time the result was considered to be positive for chlamydia. The results are listed in Table 1.

TABLE 1

ELIMINATION OF FALSE POSITIVE RESPONSES BY TREATMENT WITH HYDROGEN PEROXIDE

| Patient Patient* No. | DFA** units at result | Absorbance Result 450 nm w/o $H_2O_2$ | EIA units at w/o $H_2O_2$ | Absorbance EIA 450 nm w/ $H_2O_2$ | result w/ $H_2O_2$ |
|---|---|---|---|---|---|
| 1 | + | 1.491 | + | 1.541 | + |
| 2 | − | 0.275 | + | 0.028 | − |
| 3 | − | 0.101 | − | 0.014 | − |
| 4 | − | 0.032 | − | 0.023 | − |
| 5 | − | 0.204 | + | 0.013 | − |
| 6 | + | 0.244 | + | 0.230 | + |
| 7 | − | 0.137 | + | 0.022 | − |
| 8 | − | 0.151 | + | 0.024 | − |
| 9 | − | 0.142 | + | 0.032 | − |
| 10 | − | 0.135 | + | 0.027 | − |
| Negative Control | | 0.032 | | 0.029 | |

*Each patient specimen was noted as containing blood or blood products.
**DFA - Direct Fluorescent Assay.

In another application of this invention, an appropriate concentration of hydrogen peroxide was diluted into the buffered detergent solution used for treating patient samples. The patient swab samples were first treated with 0.5 ml of sample treatment solution without hydrogen peroxide. After removal of swab the remaining specimen was divided into two equal volumes. To one of the aliquots was added a sample treatment solution with hydrogen peroxide, to the other an equal volume of sample without hydrogen peroxide was added. The results are shown in Table 2.

TABLE 2

ELIMINATION OF FALSE POSITIVE RESPONSES BY TREATMENT WITH HYDROGEN PEROXIDE

| Patient Patient* No. | DFA** units at result | Absorbance Result 450 nm w/o $H_2O_2$ | EIA units at w/o $H_2O_2$ | Absorbance EIA 450 nm w/ $H_2O_2$ | result w/ $H_2O_2$ |
|---|---|---|---|---|---|
| 1 | + | 0.772 | + | 0.626 | + |
| 2 | + | 0.217 | + | 0.200 | + |
| 3 | − | 0.096 | − | 0.026 | − |
| 4 | − | 0.098 | − | 0.014 | − |
| 5 | − | 0.096 | − | 0.068 | − |
| 6 | − | 0.110 | − | 0.027 | − |
| 7 | − | 0.150 | + | 0.016 | − |
| 8 | − | 0.128 | + | 0.024 | − |
| 9 | + | 1.093 | + | 1.070 | + |
| 10 | + | 1.334 | + | 1.297 | + |
| Negative Control | | 0.022 | | 0.015 | |

*Each patient specimen was noted as containing blood or blood products.
**DFA - Direct Fluorescent Assay.

The oxidizing agents effective in the method of this invention include sodium hypochlorite, sodium metaperiodate, and hydrogen peroxide and other oxidizing agents that are sufficiently reactive with blood or blood products to substantially eliminate interference in a peroxidase-catalyzed, enzyme assay caused thereby. The concentration of oxidants added to the sample may be widely varied so long as it exceeds a particular minimum. Usually a solution of at least about 0.3% volume/volume ("v/v") of hydrogen peroxide can be used. Amounts in excess of 1.0% v/v of hydrogen peroxide are usually not required.

The invention is further demonstrated by the following illustrative, non limiting examples.

EXAMPLE 1

0.1ml of 3.0% v/v hydrogen peroxide solution was placed in a 12×75 mm test tube. A urogenital swab specimen was placed into the test tube and extracted by adding to the test tube 1.0 ml of a sample treatment solution containing 0.2M Tris (hydroxymethyl)-amino methane hydrochloride ("Tris HCl") a pH 8.0, 0.1M sodium chloride, 0.005M disodium ethylene diamine tetraacetic acid ($Na_2EDTA$) and 0.05% weight/volume 3-[(3-cholamido- propyl)-diamethyl ammonio]-1-propane sulfonate (CHAPS)) to the test tube. The swab was allowed to incubate in the sample treatment solution for at least 10 minutes. The tube was vortexed for 30 seconds. The swab was expressed against the side of the tube, discarded and an appropriate volume of the sample was removed from the tube for use in a chlamydia specific EIA as described in Example 4.

Example 2

A urogenital swab specimen was placed in a 12×75 mm glass test tube. A 1.0 ml volume of sample treatment solution (see example 1) containing 0.3% v/v hydrogen peroxide was added to the tube to extract the sample from the swab.

The swab was allowed to incubate in the above-described solution for at least ten minutes, vortexed, wrung out against the side of the tube to expel absorbed liquid and discarded. An appropriate volume of sample was removed from the tube for assay in a chlamydia specific EIA as described in Example 4.

EXAMPLE 3

A urogenital swab specimen was placed in a 12×75 mm test tube and extracted into 1.0 ml of the sample treatment solution of Example 1. The swab was allowed to incubate in that solution for at least 10 minutes and the tube was then vortexed for about 30 seconds. After the swab was expressed, 0.1 ml of 3.0% v/v hydrogen peroxide was added to the sample and the tube was vortexed for another ten seconds. An appropriate volume of sample was removed from the tube for use in a chlamydia specific EIA as described in Example 4.

Example 4

Two hundred microliters of the pretreated specimen, and a positive and a negative control were added to separate respective antibody coated assay tubes. The tubes were shaken gently and allowed to incubate at room temperature for about one hour.

0.1 ml of polyclonal antibody specific for chlamydia, produced and purified using well known procedures equivalent to those described in H.D. Caldwell, C. Kuo, and G.E. Kenny, 115 *Journal of Immunology*, pps. 969–975 (1975), was added to each tube, and each tube was gently mixed and allowed to incubate for an hour at room temperature.

0.1 ml of horseradish peroxidase (HRP) conjugated to antibody directed against the chlamydia-specific polyclonal antibody, available from commercial sources, was then added to each tube. Each tube was gently shaken and allowed to incubate for one hour at room temperature. The mixture in each tube was the removed and the tube washed thoroughly with deionized water.

0.5 ml of freshly prepared substrate solution consisting of one part chromogen (3.0mg/ml tetramethyl benzidine in 0.1M HCl) to 25 parts substrate buffer (0.05M sodium citrate, 0.05M boric acid, 0.012% v/v hydrogen peroxide, pH 4.2) was added to each tube, the enzyme reaction was allowed to proceed for 15 minutes and stopped with 1.0 ml of 1.0N sulfuric acid ($H_2SO_4$). Signal generation (color/formation) was measured by measuring the absorbance of the samples spectrophotometrically at 450 nm. The color intensity is a function of the amount of chlamydia antigen present in the sample and the preserve of antigen was determined accordingly. The results are set forth above in Table 1.

While a preferred embodiment of the present invention has been described, it should be understood that various changes, adaptations and modifications may be made therein without departing from the spirit of the invention and the scope of the appended claims.

What is claimed is:

1. A method for detecting the presence of an analyte using a peroxidase-catalyzed enzyme assay, the method comprising the steps of:
   (a) providing a clinical specimen suspected of containing the analyte and containing blood or blood products; and
   (b) reducing the occurrence of falsely elevated assay results by reacting the specimen with an amount of an oxidizing agent sufficient to eliminate interference in the assay caused by the blood or blood products; and subsequently
   (c) detecting the analyte in the specimen with which the oxidizing agent was reacted in the peroxidase - catalyzed enzyme assay.

2. The method of claim 1 in which the oxidizing agent is sodium hypochlorite, hydrogen peroxide or sodium meta-periodate.

3. The method of claim 1 wherein the analyte being detected is a chlamydial antigen.

4. The method of claim 1 wherein the enzyme assay is an immunoassay.

5. The method of claim 4 wherein the immunoassay is a sandwich assay.

6. The method of claim 5 wherein the sandwich assay is a capture-dependent assay.

7. A method for detecting the presence of an analyte using a peroxidase-catalyzed sandwich enzyme immunoassay the method comprising the steps of:
   (a) providing a clinical specimen suspected of containing analyte and containing blood or blood products;
   (b) reducing the occurrence of falsely elevated assay results by reacting the specimen with a sufficient amount of sodium hypochlorite to eliminate interference in the immunoassay caused by the blood or blood products; and subsequently
   (c) detecting the analyte in the specimen with which the sodium hypochlorite was reacted in the peroxidase - catalyzed sandwich enzyme immunoassay.

8. A method for detecting the presence of an analyte using a peroxidase-catalyzed sandwich enzyme immunoassay the method comprising the steps of:
   (a) providing a clinical specimen suspected of containing analyte and containing blood or blood products; and
   (b) reducing the occurrence of falsely elevated assay results by reacting the specimen with a sufficient amount of hydrogen peroxide to eliminate interference in the immunoassay caused by the blood or blood products; and subsequently
   (c) detecting the analyte in the specimen with which the hydrogen peroxide was reacted in the peroxidase-catalyzed sandwich enzyme immunoassay.

9. The method of claim 1 wherein the peroxidase is horseradish peroxidase.

* * * * *